United States Patent [19]

Hatanaka et al.

[11] Patent Number: 5,306,757
[45] Date of Patent: Apr. 26, 1994

[54] EMULSIFIED ALKENYLSUCCINIC ACID SIZING AGENT

[75] Inventors: Shigeto Hatanaka; Yoshio Takahashi; Hideto Umekawa, all of Kanagawa, Japan

[73] Assignee: Mitsubishi Oil Co., Ltd., Tokyo, Japan

[21] Appl. No.: 994,521

[22] Filed: Dec. 21, 1992

[30] Foreign Application Priority Data

Dec. 20, 1991 [JP] Japan .................. 3-354275

[51] Int. Cl.⁵ .............................. C08K 5/09
[52] U.S. Cl. ...................... 524/321; 524/112; 524/503; 524/517; 524/531; 524/557
[58] Field of Search ............... 524/112, 321, 517, 531, 524/503, 557

[56] References Cited

U.S. PATENT DOCUMENTS 3,821,069  1/1974  Wurzburg ............. 162/158
4,514,229  4/1985  Sato et al. ............ 524/112

FOREIGN PATENT DOCUMENTS 0468280  1/1992  European Pat. Off. .
2137613  10/1984  United Kingdom .

OTHER PUBLICATIONS

Database WPIL, Section Ch, Week 8505, Derwert Publications Ltd., London, GB; Class A97, AN 85-028420 and JP-A-59 223 398 (Seiko Chem Ind KK et al.). Dec. 15, 1984, abstract.

*Primary Examiner*—J. M. Reddick
*Attorney, Agent, or Firm*—Sughrue, Mion, Zinn, Macpeak & Seas

[57] ABSTRACT

Disclosed is an emulsified alkenylsuccinic acid sizing agent useful for acid papermaking. The sizing agent has a solid concentration of at least 25% by weight and comprises an alkenylsuccinic acid which is the reaction product of a branched internal olefin and maleic anhydride and which has been dispersed in water by an emulsifying and dispersing agent comprising polyvinyl alcohol. The sizing agent results in good storage stability and has an excellent sizing effect at a low addition ratio immediately after completion of high-temperature papermaking and over a wide pH range.

4 Claims, No Drawings

EMULSIFIED ALKENYLSUCCINIC ACID SIZING AGENT

FIELD OF THE INVENTION

The present invention relates to a novel alkenylsuccinic acid type emulsified sizing agent which is stable when stored at a high concentration and produces remarkable efficiency in paper sizing.

BACKGROUND OF THE INVENTION

Saponification type (or solution type) rosin sizing agents have been employed for a long time as an internal paper sizing agent in so-called acid papermaking with aluminum sulfate. It is known, however, that these sizing agents produce limited sizing effects at a low addition rate and that the sizing effects are decreased at higher water temperatures in a closed drainage system, which has been employed in recent years, or within an almost neutral pH range. In order to improve the essential disadvantages of these rosin sizing agents as described above, dispersed rosin sizing agents have been developed. However, they exert only limited sizing effects at a low addition rate and, therefore, are not satisfactory.

In order to overcome the disadvantages of these rosin sizing agents, sizing agents obtained from alkali-saponification of alkenylsuccinic acids have been used in recent years that are excellent in sizing effect at a low addition ratio (refer to JP-A-58-214598; the term "JP-A" as used herein means an "unexamined published Japanese patent application"). However, they are deficient because the sizing effects deteriorate during high-temperature papermaking or within an almost neutral papermaking pH range (e.g., 5.5 to 7.0), similar to the above-mentioned saponified rosin-series agents.

Regarding production of an emulsion-type alkenylsuccinic acid sizing agent, one known method comprises an alkenylsuccinic anhydride blended with an emulsifier and emulsified in a cationized starch solution, or water, at a low concentration of from 0.5 to 3%. The product thus obtained is used as a sizing agent for neutral paper, defined as paper with a neutral pH range (refer to U.S. Pat. No. 3,821,069).

The chemical mechanism of an alkenylsuccinic anhydride in neutral papermaking proceeds as follows. Namely, an anhydride group of the alkenylsuccinic anhydride directly reacts with a hydroxyl group of pulp resulting in a sizing effect, which is fixed on pulp fibers. In conventional neutral papermaking, therefore, an alkenylsuccinic anhydride should be added to a pulp slurry in the form of the anhydride. When previously emulsified and dispersed in water, however the alkenylsuccinic anhydride, which is highly reactive with water too, would react with water within several hours to several days and thus lose the acid anhydride group. As a result, the alkenylsuccinic anhydride not only loses its neutral sizing agent function, but also suffers from changes in the emulsion state during the course of the conversion into the corresponding alkenylsuccinic acid. This conversion causes aggregation, precipitation and separation. When used in neutral papermaking, thus, an alkenylsuccinic anhydride emulsion sizing agent in the form of an aqueous dispersion can only be stored for several hours. Accordingly, there is a technical problem because (1) it cannot be supplied in the form of a commercial product that has been formerly formulated into an emulsion of a high concentration; and (2) it should be emulsified and dispersed with the use of an emulsifying machine immediately before the papermaking. When used in an acidic region with aluminum sulfate as a fixing agent, furthermore, the alkenylsuccinic anhydride emulsion sizing agent is deficient because the sizing effect requires several days for its improvement to a sufficient level. Therefore a poor sizing effect is obtained immediately after the papermaking.

As described above, a conventional alkenylsuccinic anhydride emulsion imparts a poor sizing effect immediately after acid papermaking. This results because the emulsion sizing agent is fixed on pulp fibers in the form of the acid anhydride, and yet the alkenylsuccinic anhydride reacts slowly with the pulp within an acidic region. In addition, alkenylsuccinic anhydride appears to require a long time to react with water, form the corresponding alkenylsuccinic acid, and then further reacts with the aluminum sulfate to produce the sizing effect. It is, therefore, expected that when an alkenylsuccinic anhydride is previously converted into the corresponding alkenylsuccinic acid and emulsified, reaction with the aluminum sulfate can quickly proceed and thus a good sizing effect can be obtained even in an acidic region.

However, an alkenylsuccinic acid is highly hydrophilic, which makes it very difficult to emulsify. Thus it is very difficult in the prior art to obtain an emulsion which has a high concentration and can be stored for a long period of time without separating. When an alkenylsuccinic anhydride is emulsified by the conventional method described above, the alkenylsuccinic anhydride reacts with water in the emulsion to form an alkenylsuccinic acid, which results in an emulsion of the alkenylsuccinic acid. However, the emulsion state is changed during the course of the conversion of the alkenylsuccinic anhydride into the alkenylsuccinic acid and, therefore, no stable emulsion of the alkenylsuccinic acid can be obtained. That is to say, even though an emulsion of the alkenylsuccinic anhydride of a high concentration could be formed tentatively, the alkenylsuccinic anhydride would react with water in the emulsion and thus form an alkenylsuccinic acid while simultaneously causing aggregation, precipitation and separation and, therefore, the emulsion can never be maintained in a stable state. Thus, no stable emulsion containing an alkenylsuccinic acid at a high concentration can be obtained.

SUMMARY OF THE INVENTION

Thus, the present invention overcomes the above-mentioned disadvantages of the saponified alkenylsuccinic acid type sizing agents and alkenylsuccinic anhydride emulsion sizing agents by providing a novel alkenylsuccinic acid emulsion sizing agent having good storage stability at high concentrations and resulting in an excellent sizing effect at a low addition rate immediately after the papermaking, even during high-temperature papermaking and over a wide pH range.

The present inventors have conducted extensive studies in order to solve the above-mentioned problems and to fully utilize the excellent properties of an alkenylsuccinic acid as a starting material for a sizing agent in an emulsion-type sizing agent. As a result, they have successfully found out that an emulsified alkenylsuccinic acid sizing agent having high storage stability at a high concentration can be produced by using polyvinyl alcohol as an emulsifying and dispersing agent.

This novel emulsion is excellent in storage stability and thus produces a good sizing effect, at a low addition rate, during high-temperature papermaking or during papermaking within an almost neutral pH range as compared to any conventional saponified alkenylsuccinic acid type sizing agent.

Accordingly, the present invention relates to an emulsified alkenylsuccinic acid sizing agent having a solid concentration of at least 25% by weight, comprising an alkenylsuccinic acid obtained from a reaction product of a branched internal olefin and maleic anhydride and which is dispersed in water by an emulsifying and dispersing agent comprising polyvinyl alcohol. In a preferred embodiment, the olefin has 12 to 18 carbon atoms.

DETAILED DESCRIPTION OF THE INVENTION

In the present invention, a reaction product of, for example, a propylene oligomer and a maleic anhydride is provided as follows:

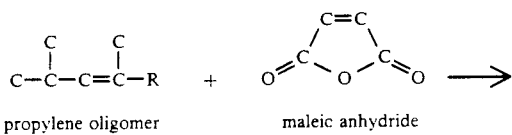

propylene oligomer       maleic anhydride where R represents additional propylene units having 6 or 12 carbon atoms.

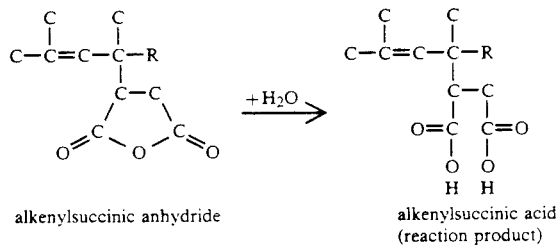

alkenylsuccinic anhydride       alkenylsuccinic acid (reaction product)

where R is as described above.

Polyvinyl alcohol is usually produced by the ester decomposition of polyvinyl acetate with an alkali. The term "polyvinyl alcohol" as used herein involves not only those compounds obtained by completely decomposing the ester into hydroxyl groups but also those partly involving acetate groups and, furthermore, so-called modified polyvinyl alcohols. The term "solid concentration" as used herein means the ratio of components other than water, based on the whole composition.

In order to produce the sizing agent of the present invention, any known emulsification method such as phase inversion emulsification or the use of a homogenizer may be selected. In particular, an alkenylsuccinic acid emulsion excellent in fineness and stability can be obtained by using a high-pressure emulsifying machine. In this case, the alkenylsuccinic acid is made molten by heating and polyvinyl alcohol dissolved in hot water is added thereto. Next, the obtained mixture is pre-emulsified and then emulsified in a high-pressure emulsifying machine.

As the alkenylsuccinic acid to be used in the present invention, those obtained by reacting an alkenylsuccinic anhydride with an equimolar amount of water may be used. As the alkenylsuccinic anhydride, those obtained by adding an olefin to maleic anhydride may be used. It is preferable to use a branched internal olefin having from 12 to 18 carbon atoms as the olefin, since an excellent sizing effect can then be obtained. Although an alkenylsuccinic acid obtained by using a straight-chain olefin as a starting material is inferior in sizing effect, it may be partly blended with an alkenylsuccinic acid that is the product of mixing equimolar amounts of water with an alkenylsuccinic anhydride formed by reacting a branched olefin with a maleic anhydride, so long as the effects of the present invention are not deteriorated thereby.

As the polyvinyl alcohol to be used in the present invention, those having a degree of polymerization of from 300 to 3,000 and a degree of saponification of from 70 to 100% by mol may be used. Those having a degree of polymerization of from 1,000 to 2,000 and a degree of saponification of from 80 to 95% by mol are particularly excellent in dispersion performance and thus preferable. Further, so-called modified polyvinyl alcohols obtained by introducing carboxyl groups into polyvinyl alcohol are also usable. A modified polyvinyl alcohol having a carboxyl group as a side chain of the polymer is preferred.

In the emulsification stage, the polyvinyl alcohol to be used as an emulsifying and dispersing agent in the present invention may be used together with other emulsifiers or polymer emulsifying and dispersing agents. Examples of the emulsifiers include anionic surfactants such as alkylbenzenesulfonic acid salts, polyoxyethylene alkyl ether sulfate salts, polyoxyethylene alkylphenyl ether sulfate salts, polyoxyethylene aralkylphenyl ether sulfate salts, alkyl ether sulfate salts, polyoxyethylene alkyl ether phosphates and salts thereof, polyoxyethylene alkylphenyl ether phosphates and salts thereof and polyoxyethylene aralkylphenyl ether phosphates and salts thereof. Examples of the emulsifiers also include nonionic surfactants such as polyoxyethylene alkyl ethers, polyoxyethylene alkylphenyl ethers, polyoxyethylene aralkylphenyl ethers, sorbitan fatty acid esters and polyoxyethylene sorbitan fatty acid esters. Examples of the polymer emulsifying and dispersing agents include anionic agents, such as a copolymer comprising a component (A) which is a monomer constituting a hydrophilic group and another component (B) which is a monomer constituting a hydrophobic group and its partially or completely saponified products. Examples of the component (A) include acrylic acid, methacrylic acid, maleic acid, maleic anhydride, itaconic acid and fumaric acid, while examples of the component (B) include styrene-series monomers such as styrene and α-methylstyrene, acryl esters and methacryl esters such as methyl acrylate, methyl methacrylate, ethyl acrylate, ethyl methacrylate, butyl acrylate and butyl methacrylate and (meth)acrylamides and acrylonitrile.

Further, a hydrocarbon resin free from any acid group may be blended with the alkenylsuccinic acid in order to improve the emulsion properties and the stability of the emulsion. In this case, the alkenylsuccinic acid functions as a hydrophobic compound which imparts a sizing effect, and the hydrocarbon resin functions to improve emulsion stability and to make the particle size of an emulsion small for good diffusibility. In this case, the resin may be selected from among, for example, aromatic methylene resins and aromatic formaldehyde resins wherein aromatic rings are bound to each other via methylene, ether, acetal or methylol groups. From 25 to 95 parts by weight of the alkenylsuccinic acid may be blended with from 75 to 5 parts by weight of the acid group-free hydrocarbon resin.

The composition may further contain, if needed, other resinous materials such as rosin and modified rosins such as products obtained by reacting rosin with $\alpha\beta$-unsaturated polybasic acids, disproportionate rosin, polymerized rosin, hydrogenated rosin, products obtained by reacting rosin with formaldehyde, fatty acids, tall oil, paraffin wax or petroleum hydrocarbons. In such a case, it is preferable that the total content of the alkenylsuccinic acid or the mixture of the alkenylsuccinic acid with the acid group-free hydrocarbon resin in said composition amounts to at least 50% by weight. That is to say, it is not preferable that the content of the resinous materials, other than the alkenylsuccinic acid or the mixture of the alkenylsuccinic acid with the acid group-free hydrocarbon resin, in said composition exceeds 50% by weight, since the sizing effect is deteriorated in this case.

When the alkenylsuccinic acid is replaced with an alkenylsuccinic anhydride and the emulsification is performed in the same manner, an aqueous emulsion containing an alkenylsuccinic anhydride can be obtained. In this case, though, the alkenylsuccinic anhydride would be converted into the corresponding alkenylsuccinic acid after 1 to 2 days via a reaction with the water in the emulsion. When an emulsifying and dispersing agent comprising polyvinyl alcohol, which is the characteristic feature of the present invention, is used, the emulsion state is never changed during the course of the conversion of the alkenylsuccinic anhydride into the alkenylsuccinic acid. As a result, a sizing agent of the present invention which contains the alkenylsuccinic acid in a stable form can be obtained without causing aggregation, precipitation or separation. Although the alkenylsuccinic anhydride may be emulsified alone in this case, a more stable sizing agent can be obtained by blending an acid group-free hydrocarbon resin therewith, as described in Japanese Patent Application No. 03-196962.

The polyvinyl alcohol may be used at a ratio of from 1 to 20 parts by weight, preferably from 2 to 5 parts by weight, per 100 parts by weight of the alkenylsuccinic acid. When an acid group-free hydrocarbon resin and other resinous materials such as rosin are further blended in addition to the alkenylsuccinic acid, the polyvinyl alcohol may be used in an amount of from 1 to 20 parts by weight per 100 parts by weight of the total amount of the alkenylsuccinic acid, the acid-free hydrocarbon resin and the resinous materials.

Further, modified products of alkenylsuccinic acids such as alkali metal salts, amine salts, esters, imides or amides may be added thereto, though they scarcely contribute to the sizing effect.

Since the polyvinyl alcohol to be used as an emulsifying and dispersing agent in the present invention is nonionic, cationic, nonionic, anionic or amphoteric water-soluble polymers may be blended after the completion of the emulsification in order to elevate the fixing ratio of the sizing agent. As an example of these polymers, an acrylamide-series polymer may be cited. The molecular weight of the polymer may preferably range from 100,000 to 800,000. The blending ratio of the polymer may be arbitrarily selected. However, it is recommended in practice to use from 1 to 50 parts by weight of the polymer, in terms of solid matter, per 100 parts by weight of the alkenylsuccinic acid (plus other resinous materials, if contained), since the addition of an excess amount of the polymer lowers the concentration of the effective component in the sizing agent. In particular, when a cationic or amphoteric polymer is added, the obtained sizing agent shows a good sizing effect at a relatively high pH value (i.e., pH 5.5 to 7).

The sizing agent according to the present invention may be added at an arbitrary step prior to the completion of the papermaking procedure, as are conventional rosin-series sizing agents. For example, aluminum sulfate may be added to a pulp slurry during or after the beating stage either before or after adding the sizing agent of the present invention to thereby adjust the pH value of the slurry to 4.0 to 7.0, thus fixing the sizing agent to the pulp. Furthermore, the sizing agent of the present invention may be used optionally together with conventional rosin-series sizing agents or petroleum resin agents in an arbitrary ratio.

In the case of the internal sizing, the sizing agent according to the present invention may be used (added) in an amount of from 0.01 to 5.0% by weight, preferably from 0.05 to 3.0% by weight, based on the weight of the dry pulp.

To further illustrate the present invention in greater detail, and not by way of limitation, the following Examples and Comparative Examples will be given. Unless otherwise noted, all "parts" are by weight.

EXAMPLE 1

An alkenylsuccinic anhydride, which was obtained via an addition reaction of a propylene oligomer (average carbon atom number: 15) with maleic anhydride, was reacted with an equimolar amount of water to give an alkenylsuccinic acid. One hundred parts of this alkenylsuccinic acid were heated to 90° C., and a solution of 3 parts of polyvinyl alcohol (Poval PVA-217; manufactured by Kuraray Co., Ltd., degree of polymerization: about 1,700, degree of saponification: 88% by mol) dissolved in 155 parts of water was heated to 90° C. and added to the heated acid, followed by mixing. Subsequently, the emulsion thus obtained was homogenized by passing a piston high pressure emulsifying machine (manufactured by APV-Gaulin Co.) under a pressure of 300 kg/cm$^2$ twice. Then it was quickly cooled to room temperature and thus an oil-in-water type emulsion of a total solid content of 40% by weight was obtained.

EXAMPLE 2

An alkenylsuccinic anhydride, which was obtained via an addition reaction of a propylene oligomer (average carbon atom number: 18) with maleic anhydride, was reacted with an equimolar amount of water to thereby give an alkenylsuccinic acid. One hundred parts of this alkenylsuccinic acid were heated to 90° C., and a solution of 5 parts of polyvinyl alcohol (Gosenol C-500, manufactured by The Nippon Synthetic Chemical Industry, Co., Ltd., degree of polymerization: about 1,500, degree of saponification: 96% by mol) dissolved in 158 parts of water was heated to 90° C. and added to the heated acid, followed by mixing. Subsequently, the mixture thus obtained was emulsified by stirring in a homomixer (model TK, manufactured by Tokushu Kika Kogyo K.K.) at 10,000 rpm for 2 minutes and thus an oil-in-water type emulsion of a total solid content of 40% by weight was obtained.

EXAMPLE 3

An alkenylsuccinic anhydride, which was obtained via an addition reaction of a propylene oligomer (average carbon atom number: 12) with maleic anhydride, was reacted with an equimolar amount of water to thereby give an alkenylsuccinic acid. At 70° C., 80 parts of this alkenylsuccinic acid was mixed with 20 parts of an aromatic methylene resin (Oligotech 1300, manufactured by Mitsubishi Oil Co., Ltd., average molecular weight: 700) and 5 parts of polyoxyethylene (degree of polymerization: 17) nonylphenyl ether phosphate. To the obtained mixture, a solution of 10 parts of polyvinyl alcohol (Gosenol KM-17, manufactured by The Nippon Synthetic Chemical Industry, Co., Ltd., degree of polymerization: about 1,700, degree of saponification: 80% by mol) dissolved in 173 parts of water was slowly added at 70° C. After phase inversion emulsification, an oil-in-water type emulsion of a total solid content of 40% by weight was obtained.

EXAMPLE 4

Eighty parts of an alkenylsuccinic anhydride, which were obtained via an addition reaction of an n-butene oligomer (average carbon atom number: 16) with maleic anhydride, were mixed with 20 parts of an aromatic methylene resin (Oligotech 1300, manufactured by Mitsubishi Oil Co., Ltd., average molecular weight: 700), and 4 parts of polyoxyethylene (degree of polymerization: 17) nonylphenyl ether phosphate, 3 parts of polyoxyethylene (degree of polymerization: 4) nonylphenyl ether sulfate ammonium and 2 parts of oleic acid were further added thereto. To the obtained mixture, a solution of 10 parts of anion-modified polyvinyl alcohol (Gosenal T-350, manufactured by The Nippon Synthetic Chemical Industry, Co., Ltd., degree of polymerization: about 1,500, degree of saponification: 94% by mol) dissolved in 180 parts of water was slowly added. After phase inversion emulsification, an oil-in-water type emulsion of a total solid content of 40% by weight was obtained.

EXAMPLE 5

An alkenylsuccinic anhydride, which was obtained via an addition reaction of a propylene oligomer (average carbon atom number: 15) with maleic anhydride, was reacted with an equimolar amount of water to thereby give an alkenylsuccinic acid. Eighty parts of this alkenylsuccinic acid were mixed with 20 parts of tall oil (SR-30, manufactured by Harima Chemicals, Inc.). The mixture thus obtained was heated to 90° C., and a solution of 3 parts of block-copolymerization type polyvinyl alcohol (Poval PVA-217; manufactured by Kuraray Co., Ltd., degree of polymerization: about 1,700, degree of saponification: 88% by mol) dissolved in 155 parts of water was heated to 90° C. and added to the heated mixture, followed by mixing. Subsequently, the emulsion thus obtained was homogenized by passing a piston high pressure emulsifying machine (manufactured by APV-Gaulin Co.) under a pressure of 300 kg/cm$^2$ twice. Then it was quickly cooled to room temperature and thus an oil-in-water type emulsion of a total solid content of 40% by weight was obtained.

EXAMPLE 6

An alkenylsuccinic anhydride, which was obtained via an addition reaction of a propylene oligomer (average carbon atom number: 15) with maleic anhydride, was reacted with an equimolar amount of water to thereby give an alkenylsuccinic acid. Eighty parts of this alkenylsuccinic acid were mixed with 20 parts of tall oil (SR-30, manufactured by Harima Chemicals, Inc.). The mixture thus obtained was heated to 90° C., and a solution of 3 parts of polyvinyl alcohol (Gosenol GH-17, manufactured by The Nippon Synthetic Chemical Industry, Co., Ltd., degree of polymerization: about 1,700, degree of saponification: 88% by mol) dissolved in 155 parts of water was heated to 90° C. and added thereto, followed by mixing. Subsequently, the emulsion thus obtained was homogenized by passing a piston high pressure emulsifying machine (manufactured by APV-Gaulin Co.) under a pressure of 300 kg/cm$^2$ twice. Then it was quickly cooled to room temperature and thus an oil-in-water type emulsion of a total solid content of 40% by weight was obtained.

EXAMPLE 7

One hundred parts of the emulsion prepared in the above Example 6 was mixed with 15 parts of a commercially available anionic acrylamide-series polymer having a solid content of 15% (Polyacron V, manufactured by Misawa Ceramic Chemical K.K.) to give an oil-in-water emulsion of a total solid content of 37% by weight.

EXAMPLE 8

Eighty-five parts of acrylamide, 11 parts of N,N-dimethylpropylaminoacrylamide, 4 parts of maleic acid, 4 parts of 1% 2-mercaptoethanol, 5 parts of phosphoric acid, 5 parts of 10% ammonium persulfate and 590 parts of water were mixed together and polymerized with stirring at 80° C. for 2 hours. The amphoteric acrylamide polymer thus obtained had a solid content of 15% by weight and a weight-average molecular weight of 400,000. Fifteen parts of this polymer were mixed with 100 parts of the emulsion prepared in the above Example 6 to thereby give an oil-in-water type emulsion of a total solid content of 37% by weight.

COMPARATIVE EXAMPLE 1

A commercially available dispersed rosin sizing agent having a solid content of 50%, which was produced by emulsifying components comprising rosin fumarate as the main component with a polymer emulsifying and dispersing agent, (TO-500J, manufactured by Dick Hercules Co.), was employed.

COMPARATIVE EXAMPLE 2

A commercially available saponified rosin sizing agent of a solid content of 50%, which was produced by saponifying components comprising rosin maleate as the main component with caustic potash, (PF Size 800L, manufactured by Misawa Ceramic Chemical K.K.), was employed.

COMPARATIVE EXAMPLE 3

To 100 parts of an alkenylsuccinic anhydride, which was obtained via an addition reaction of a propylene oligomer (average carbon atom number: 15) with maleic anhydride, were added 5 parts of polyoxyethylene (degree of polymerization: 13) nonylphenyl ether. After thoroughly stirring at 50° C., 1 part of this mixture was mixed with 99 parts of water and emulsified by stirring in a homomixer at 10,000 rpm for 1 minute. Thus, an oil-in-water type emulsion of a total solid content of 1% by weight was obtained.

COMPARATIVE EXAMPLE 4

To 100 parts of an alkenylsuccinic anhydride, which was obtained via an addition reaction of a straight-chain internal olefin (average carbon atom number: 16) with maleic anhydride, were added 5 parts of polyoxyethylene (degree of polymerization: 13) nonylphenyl ether. After thoroughly stirring at 50° C., 1 part of this mixture was mixed with 99 parts of water and emulsified by stirring in a homomixer at 10,000 rpm for 1 minute. Thus, an oil-in-water type emulsion of a total solid content of 1% by weight was obtained.

COMPARATIVE EXAMPLE 5

To 80 parts of an alkenylsuccinic anhydride, which was obtained via an addition reaction of a straight-chain internal olefin (average carbon atom number: 16) with maleic anhydride, were added 20 parts of a commercially available aromatic methylene resin (Oligotech 1300, manufactured by Mitsubishi Oil Co., Ltd., average molecular weight: 700), and 4 parts of polyoxyethylene (degree of polymerization: 17) nonylphenyl ether phosphate, 3 parts of polyoxyethylene (degree of polymerization: 4) nonylphenyl ether sulfate ammonium and 2 parts of oleic acid were further added thereto. To the obtained mixture, a solution of 10 parts of anion-modified polyvinyl alcohol (Gosenal T-350, manufactured by The Nippon Synthetic Chemical Industry, Co., Ltd., degree of polymerization: about 1,500, degree of saponification: 94% by mol) dissolved in 180 parts of water was slowly added. After phase inversion emulsification, an oil-in-water type emulsion having a total solid content of 40% by weight was obtained.

COMPARATIVE EXAMPLE 6

An alkenylsuccinic anhydride, which was obtained via an addition reaction of a propylene oligomer (average carbon atom number: 15) with maleic anhydride, was reacted with an equimolar amount of water to thereby give an alkenylsuccinic acid. One hundred parts of this alkenylsuccinic acid were heated to 90° C., and a solution of 5 parts of polyoxyethylcne (degree of polymerization: 13) nonylphenyl ether dissolved in 155 parts of water was heated to 90° C. and slowly added to the heated acid, followed by mixing. Subsequently, the emulsion thus obtained was homogenized by passing a piston high pressure emulsifying machine (manufactured by APV-Gaulin Co.) under a pressure of 300 kg/cm² twice. Then it was quickly cooled to room temperature, and thus an oil-in-water type emulsion of a total solid content of 40% by weight was obtained.

COMPARATIVE EXAMPLE 7

To 60 parts of an alkenylsuccinic anhydride, which was obtained via an addition reaction of a propylene oligomer (average carbon atom number: 12) with maleic anhydride, was added a solution of 26 parts of potassium hydroxide dissolved in 126 parts of water. The mixture was maintained at a temperature of 90° to 100° C. and stirred. After 3 hours, it was cooled to room temperature, and thus a saponified alkenylsuccinic acid type sizing agent of a total solid content of 40% by weight was obtained.

Storage Stability Test

Twenty-five g of each of the emulsified alkenylsuccinic acid sizing agents prepared in accordance with the methods described in Examples 1 to 8, a commercially available sizing agent of Comparative Example 1 and emulsified alkenylsuccinic acid sizing agents prepared in the Comparative Examples 3, 4, 5 and 6 was introduced into a glass bottle (50 ml) and allowed to stand at room temperature (25° C.). Then its stability was observed with the naked eye after 1, 7 and 60 days. A sample having a poor storage stability showed the separation or precipitation of oily matters at the bottom of the bottle or at the upper part of the emulsion. No storage stability test was carried out on the products of Comparative Examples 2 and 7, since they were not emulsion-type sizing agents but saponified agents.

Table 1 summarizes the results.

Sizing Effect Test

A bleached kraft pulp (LBKP, bleached hard wood pulp) was diluted with tap water to give a pulp concentration of 2.5% and then beaten with a beater to thereby give a Canadian freeness of about 450 ml. The pulp slurry thus obtained was then formulated into a slurry of a concentration of 2.0% by weight with tap water at 50° C. and aluminum sulfate (1.0% by weight based on the pulp) was added thereto under stirring. After diluting to a concentration of 0.5% by weight with water of pH 4.5 at 50° C., each of the sizing agents (0.3% by weight based on the pulp) of Examples 1 to 8 and Comparative Examples 1 to 7 was added thereto. After papermaking with a TAPPI standard machine (paper weight: 60 g/m²), the moist paper thus obtained was pressed and dried in a conventional manner. Immediately after the paper thus obtained was dried and after the paper thus obtained was then subjected to moisture conditioning in a thermostatic moist room at a temperature of 20° C. under a relative humidity of 65% for 1 day, the sizing effect of the sizing agent was determined by the Stöckigt method in accordance with JIS P 8122.

Further, a high pH-papermaking test was carried out by adding 0.7% by weight (based on the pulp) of aluminum sulfate and adjusting the diluting water and the papermaking water to pH 6.0. The obtained products were similarly evaluated. The sizing agents of Examples 1 to 8 and the agent of Comparative Example 5 were tested 10 days after the emulsification. The alkenylsuccinic anhydride emulsion sizing agents of Comparative Examples 3, 4 and 6 were tested immediately after the completion of the emulsification, since they had poor storage stability and could not be maintained in the emulsion state 10 days after emulsification.

Table 2 summarizes the results.

TABLE 1

| | Results of Storage Stability Test | | |
| --- | --- | --- | --- |
| | Standing days | | |
| | 1 day | 7 days | 60 days |
| Example 1 | no precipitate | no precipitate | no precipitate |
| Example 2 | no precipitate | no precipitate | trace precipitate |
| Example 3 | no precipitate | no precipitate | trace precipitate |
| Example 4 | no precipitate | no precipitate | trace precipitate |
| Example 5 | no precipitate | no precipitate | no precipitate |
| Example 6 | no precipitate | no precipitate | no precipitate |
| Example 7 | no precipitate | no precipitate | no precipitate |
| Example 8 | no precipitate | no precipitate | trace precipitate |
| Comparative Example 1 | no precipitate | no precipitate | trace precipitate |
| Comparative Example 2 | — | — | — |
| Comparative Example 3 | substantial precipitate | substantial precipitate | substantial precipitate |
| Comparative Example 4 | substantial precipitate | substantial precipitate | substantial precipitate |
| Comparative | no precipitate | no precipitate | trace precipitate |

TABLE 1-continued

Results of Storage Stability Test

| | Standing days | | |
|---|---|---|---|
| | 1 day | 7 days | 60 days |
| Example 5 | | | |
| Comparative Example 6 | substantial precipitate | substantial precipitate | substantial precipitate |
| Comparative Example 7 | — | — | — |

TABLE 2

<Sizing Effect Determination>

Stockigt Sizing Degree (sec.)

| | Aluminum sulfate 1.0% Water for papermaking pH 4.5 | | Aluminum sulfate 0.7% Water for papermaking pH 6.0 | |
|---|---|---|---|---|
| | Immediately After drying | After 1 day of moisture conditioning | Immediately after drying | After 1 day of moisture conditioning |
| Example 1 | 22 | 23 | 14 | 14 |
| Example 2 | 18 | 19 | 12 | 13 |
| Example 3 | 17 | 17 | 11 | 12 |
| Example 4 | 19 | 19 | 13 | 14 |
| Example 5 | 25 | 25 | 15 | 16 |
| Example 6 | 23 | 23 | 13 | 14 |
| Example 7 | 25 | 25 | 16 | 16 |
| Example 8 | 24 | 25 | 20 | 21 |
| Comparative Example 1 | 14 | 15 | 8 | 9 |
| Comparative Example 2 | 4 | 8 | 2 | 5 |
| Comparative Example 3 | 0 | 3 | 1 | 5 |
| Comparative Example 4 | 0 | 16 | 2 | 20 |
| Comparative Example 5 | 6 | 7 | 5 | 5 |
| Comparative Example 6 | 2 | 6 | 4 | 8 |
| Comparative Example 7 | 12 | 12 | 6 | 7 |

Compared with conventional alkenylsuccinic anhydride sizing agents, the emulsified alkenylsuccinic acid sizing agents of the present invention have a high concentration and a good storage stability and exert an excellent sizing effect immediately after completion of papermaking. Further, it suffers little deterioration in sizing effect over a wide pH range in high-temperature papermaking, compared with saponified alkenylsuccinic acid type sizing agents.

While the invention has been described in detail and with reference to specific embodiments thereof, it will be apparent to one skilled in the art that various changes and modifications can be made therein without departing from the spirit and scope thereof.

What is claimed is:

1. An emulsified alkenylsuccinic acid sizing agent having a solid concentration of at least 25% by weight, said agent comprising an alkenylsuccinic acid which is the reaction product of a branched internal olefin having 12 to 18 carbon atoms and maleic anhydride and which has been emulsified and dispersed in water by polyvinyl alcohol.

2. The emulsified alkenylsuccinic acid sizing agent as claimed in claim 1, wherein the polyvinyl alcohol has a degree of polymerization of 300 to 3,000 and a degree of saponification of 70 to 100% by mol.

3. The emulsified alkenylsuccinic acid sizing agent as claimed in claim 1, wherein the polyvinyl alcohol has a degree of polymerization of 1,000 to 2,000 and a degree of saponification of 80 to 95% by mol.

4. The emulsified alkenylsuccinic acid sizing agent as claimed in claim 1, wherein the alkenylsuccinic acid is blended with an aromatic methylene resin.

* * * * *